United States Patent
Pack et al.

(10) Patent No.: US 11,633,491 B2
(45) Date of Patent: *Apr. 25, 2023

(54) LINKER COMPOSITION COMPRISING SILICA-FORMING PEPTIDES

(71) Applicant: Korea University Research and Business Foundation, Sejong Campus, Sejong (KR)

(72) Inventors: Seung Pil Pack, Seoul (KR); Mohamed Abdeltawab Abdallah Abdelhamid, Sejong (KR); Ki Baek Yeo, Busan (KR); Mi Ran Ki, Sejong (KR)

(73) Assignee: Korea University Research and Business Foundation, Sejong Campus, Sejong (KR)

( * ) Notice: Subject to any disclaimer, the term of this patent is extended or adjusted under 35 U.S.C. 154(b) by 397 days.

This patent is subject to a terminal disclaimer.

(21) Appl. No.: 16/793,081

(22) Filed: Feb. 18, 2020

(65) Prior Publication Data
US 2020/0261593 A1 Aug. 20, 2020

(30) Foreign Application Priority Data
Feb. 15, 2019 (KR) .................. 10-2019-0017807
Feb. 4, 2020 (KR) .................. 10-2020-0013232

(51) Int. Cl.
*A61K 47/65* (2017.01)
*A61K 47/64* (2017.01)

(52) U.S. Cl.
CPC ............. *A61K 47/65* (2017.08); *A61K 47/64* (2017.08)

(58) Field of Classification Search
None
See application file for complete search history.

(56) References Cited

U.S. PATENT DOCUMENTS 9,404,097 B2 * 8/2016 Pack .................... C12Y 207/01

FOREIGN PATENT DOCUMENTS

JP 4592752 B2 9/2010
KR 10-2013-0035985 A 4/2013

OTHER PUBLICATIONS

Yeo, Ki Baek et al. "Novel Silica-Forming Peptides Derived from Ectocarpus Siliculosus", Accepted Manuscript, *Process Biochemistry*, http://dx.dol.org/10.1016/i.procbio.2017.04.004, Mar. 4, 2017 (20 pages in English).
Yeo, Ki Baek, Master's Thesis, Korea University, 2013 (2 pages in English and 69 pages in Korean).
Korean Office Action dated Sep. 9, 2021, in counterpart Korean Patent Application No. 10-2020-0013232 (4 pages in Korea).
Korean Notice of Allowance dated May 16, 2022, in counterpart Korean Patent Application No. (10-2020-0013232 (5 pages in Korean).

* cited by examiner

*Primary Examiner* — Samantha L Shterengarts
(74) *Attorney, Agent, or Firm* — NSIP Law

(57) ABSTRACT

The present disclosure relates to the use of silica-forming peptides (SFPs) Volp1 and Salp1 for protein fusion tags for protein purification, silica formation and self-encapsulation, and controlled release of biomolecules. After preparing a fusion protein containing the Volp1 or Salp1 peptide at the C-terminal of the protein, the adsorption conditions for silica ($SiO_2$) surface were optimized. As a result, a high-purity fusion protein could be purified without an additional tag for purification. The fusion protein containing the silica-forming peptide was self-encapsulated and stably immobilized in the silica matrix through reaction with a silica precursor. The Volp1 and Salp1 peptides showed stronger adsorption ability for silica than the previously known R5 peptide. Using these characteristics, a silica complex wherein two proteins are encapsulated was prepared by mixing the R5 fusion protein with the Volp1 or Salp1 fusion protein. The resulting controlled release system allows the release of the R5 fusion protein in the first step and release of the Salp1 fusion protein in the second step based on the difference in adsorption affinity.

3 Claims, 8 Drawing Sheets

Specification includes a Sequence Listing.

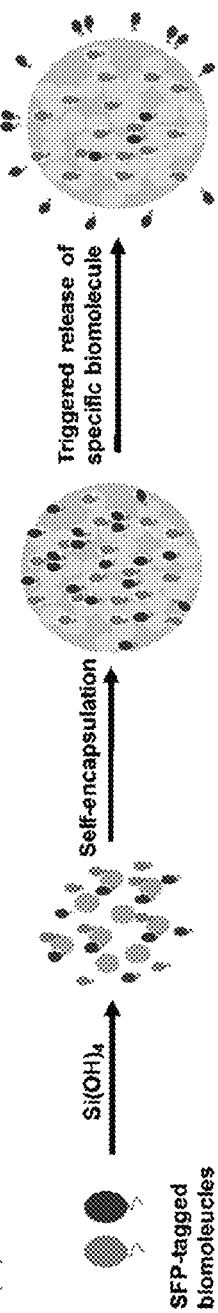
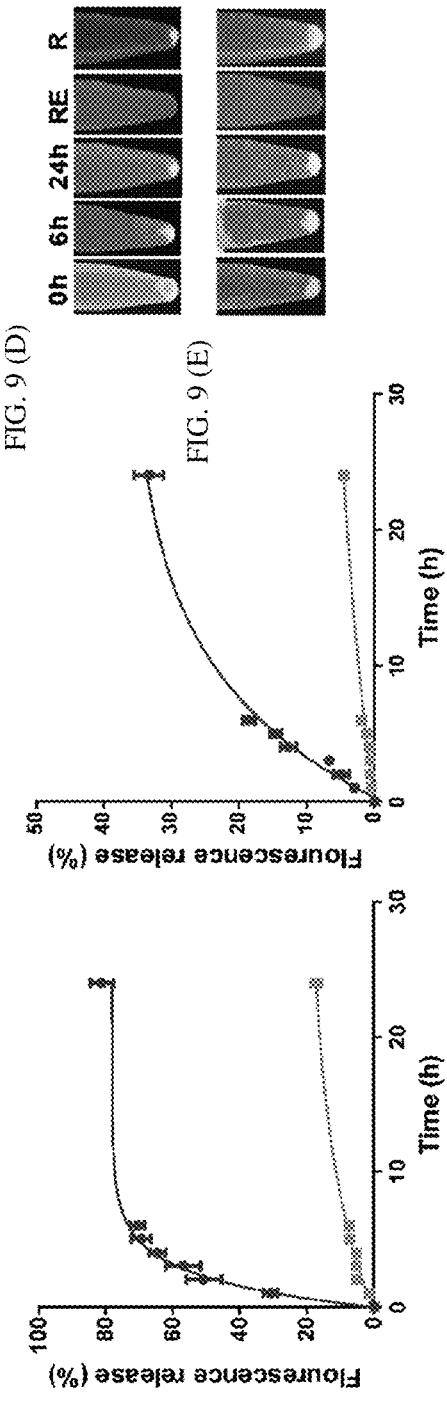
FIG. 9 (A)
FIG. 9 (B)
FIG. 9 (C)
FIG. 9 (D)
FIG. 9 (E)

LINKER COMPOSITION COMPRISING SILICA-FORMING PEPTIDES

CROSS-REFERENCE TO RELATED APPLICATIONS

This application claims the benefit under 35 USC 119(a) of Korean Patent Application No. 10-2019-0017807 filed on Feb. 15, 2019, and Korean Patent Application No. 10-2020-0013232 filed on Feb. 4, 2020 in the Korean Intellectual Property Office, the entire disclosures of which are incorporated herein by reference for all purposes.

TECHNICAL FIELD

The present disclosure relates to a linker composition containing two or more silica-forming peptides having different affinity for silica, a drug delivery system using the same, a method for isolating and purifying a target substance using the same, and so forth.

BACKGROUND ART

Silica is one of the most common biominerals existing in the earth. The external structures of diatoms or sponges are typical examples. Silica can be easily used as a biomaterial since it has good chemical stability against temperature or pH as well as mechanical strength and has excellent biocompatibility. Accordingly, the development of silica-based nanomaterials is conducted actively in the fields of drug delivery systems, enzyme immobilization, biocatalysts, etc. However, since the existing method of silica synthesis by liquid-gas synthesis (chemical silica synthesis) uses toxic chemical substances in high-temperature, high-pressure environments under strongly acidic or strongly basic pH conditions, it is limited a lot in further applications. This problem may be solved by mimicking the formation of biosilica in living organisms.

During the formation of biosilica, silicon (Si) is absorbed in the form of silicic acid and is prepared into a unique silica structure such as the needle-like structure of sponge or the shell of diatoms through precipitation. This mechanism of biosilica formation has been studied intensively. It has been found out that the protein called sponge-derived silicatein initiated silica polymerization from a silica precursor through silica polymerization, in vitro. Therefore, there has been an attempt to mimic the formation of biosilica by using a cysteine-lysine diblock copolymer similar to silicatein or a small biomolecule such as cystamine. In addition, a method of surrounding living single cells with silica using a synthetic cysteine-arginine polypeptide has been reported.

Another well-known silica-forming protein is silaffin derived from diatoms. Silaffin is characterized by its highly post-translational modifications. Such modifications play an important role in the precipitation of silica under biological conditions and help silaffin to bind strongly to the biosilica of diatoms. However, it has been found out that silica precipitation can occur for the silaffin R5 peptide, which is not post-translationally modified, under specific conditions. This has been applied to the recombinant DNA technology to fuse the silaffin R5 sequence with proteins such as glucose oxidase, phosphodiesterase, carbonic anhydrase, etc. as a short peptide tag, such that the proteins can form silica directly and are immobilized at the same time.

Researches are conducted consistently for the development of peptides forming silica under relatively mild conditions and for the development of drug delivery systems, enzyme immobilization, biocatalysts, etc. using the silica-forming peptides. The inventors of the present disclosure have discovered several silica-forming peptides derived from microalgae and marine choanoflagellates and have completed the present disclosure by consistently studying the silica adsorption ability, self-encapsulation and controlled release of target substances of the silica-forming peptides fused with the target substances.

DISCLOSURE

Technical Problem

The present disclosure is aimed to providing a linker composition containing two or more silica-forming peptides having different affinity for silica, a drug delivery system using the same, a method for preparing the same, and a method for isolating and purifying a target substance using the same.

However, the technical problem to be solved with the present disclosure is not limited to that described above. Other problems not mentioned above will be clearly understood by those of ordinary skill from the following detailed description.

Technical Solution

The present disclosure provides a linker composition containing two or more silica-forming peptides (SFPs) having different affinity for silica.

In an exemplary embodiment of the present disclosure, the composition may be used for isolation and purification of a substance bound to the silica-forming peptide, and may be used for control of the release of a substance bound to the silica-forming peptide.

In addition, the present disclosure provides a drug delivery system (DDS) including a silica complex wherein two or more silica-forming peptides having different affinity for silica are bound as an active ingredient.

In an exemplary embodiment of the present disclosure, the silica-forming peptide of the delivery system may be bound to a drug.

In another exemplary embodiment of the present disclosure, the drug may be one or more selected from a group consisting of a compound, a peptide, a protein, an imaging agent, a gene construct and a combination thereof.

In an exemplary embodiment of the present disclosure, the silica complex may be in the form of one or more selected from a group consisting of a particle, a gel and a mixture thereof.

In addition, the present disclosure provides a method for preparing a drug delivery system, which includes a step of reacting two or more silica-forming peptides with a silica precursor, and wherein the SFPs have different affinity for silica and bound to a drug.

In an exemplary embodiment of the present disclosure, the drug may be one or more selected from a group consisting of a compound, a peptide, a protein, an imaging agent, a gene construct and a combination thereof, and the drugs bound to the two silica-forming peptides may be identical to or different from each other.

In another exemplary embodiment of the present disclosure, the silica precursor may be one or more selected from a group consisting of tetraethyl orthosilicate, tetramethyl orthosilicate, methyltriethoxysilane, phenyltriethoxysilane, diethyldimethoxysilane, ethyltriethoxysilane, titanium tetraisopropoxide and tetraethylgermanium.

In addition, the present disclosure provides a method for isolating and purifying a target substance, which includes: (1) a step of preparing a solution containing two or more silica-forming peptides to which different target substances are bound; (2) a step of reacting the solution with a silica bead; and (3) a step of separating the silica bead, wherein the two or more silica-forming peptides have different affinity for silica.

In an exemplary embodiment of the present disclosure, the target substance may be a peptide or a protein, and the step (1) may include steps (a)-(c):

(a) a step of preparing a recombinant expression vector wherein genes encoding the target substance and the silica-forming peptide are introduced such that the substance and the peptide can be translated as being bound;

(b) a step of preparing a transformant wherein the recombinant expression vector is introduced; and (c) a step of culturing the transformant.

In another exemplary embodiment of the present disclosure, the method for isolating and purifying a target substance may further include, after the step (3), (4) a step of isolating the target substance bound to the peptide including an amino acid sequence of SEQ ID NO 1 or the peptide including an amino acid sequence of SEQ ID NO 2 by reacting the separated silica bead with a 0.25 M arginine solution.

In an exemplary embodiment of the present disclosure, the two or more silica-forming peptides of the step (1) may be the peptide including an amino acid sequence of SEQ ID NO 3, and the method further includes, after the step (4), (5) a step of isolating the target substance bound to the peptide comprising an amino acid sequence of SEQ ID NO 3 by reacting the silica bead with a 1 M arginine solution.

In the present disclosure, the silica-forming peptide may be selected from a group consisting of: a peptide including an amino acid sequence of SEQ ID NO 1; a peptide including an amino acid sequence of SEQ ID NO 2; and a peptide including an amino acid sequence of SEQ ID NO 3.

Advantageous Effects

The inventors of the present disclosure have identified the adsorption ability of silica-forming peptides for silica and the difference in the adsorption affinity for silica of different silica-forming peptides, and provide them as a linker that can be used for purification, self-encapsulation and controlled release of proteins. The linker of the present disclosure may be used as a tag for protein purification in order to solve the problem of the His-tag and to purify proteins with high purity without an additional tag for purification. In addition, silica can be formed under the biological environment and proteins can be immobilized through self-encapsulation. The protein immobilized in silica can advantageously maintain its activity since it is protected from abiotic stress and may be released again from the organic-inorganic composite type silica particle and/or silica gel on which the protein is immobilized through controlled release. The present disclosure allows a target protein to be recovered by inducing the release of an SFP fusion protein from silica using L-arginine single molecules. The present disclosure is advantageous in that two or more proteins can be isolated and recovered independently. Therefore, it is expected that the present disclosure can be applied to the technology of isolating a number of biomolecules immobilized in an inorganic matrix. In addition, when applied to enzymatic cascade reactions, economic efficiency may be improved since the stability of a plurality of enzymes can be maintained while they are spatially close to each other and the enzymes can be isolated and recycled after the reactions.

PBS: 25 mM sodium phosphate buffer (pH 6-6.5)
PBST: 25 mM sodium phosphate buffer (pH 6-6.5) with 0.1% Tween 20
(buffer condition during adsorption step/buffer condition during the washing step)

Figure 2:
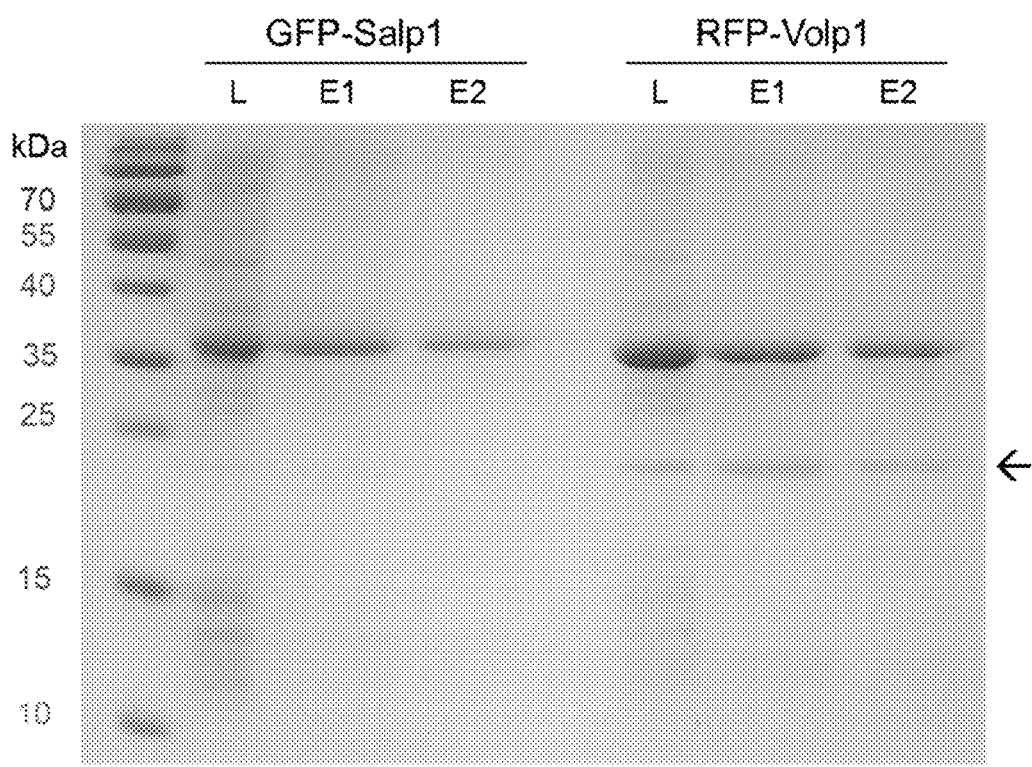

FIG. 2 shows SDS-PAGE results for Volp1 and Salp1 fusion proteins using silica particles.

L: cell lysate, E1: elution 1, E2: elution 2

Figure 3:
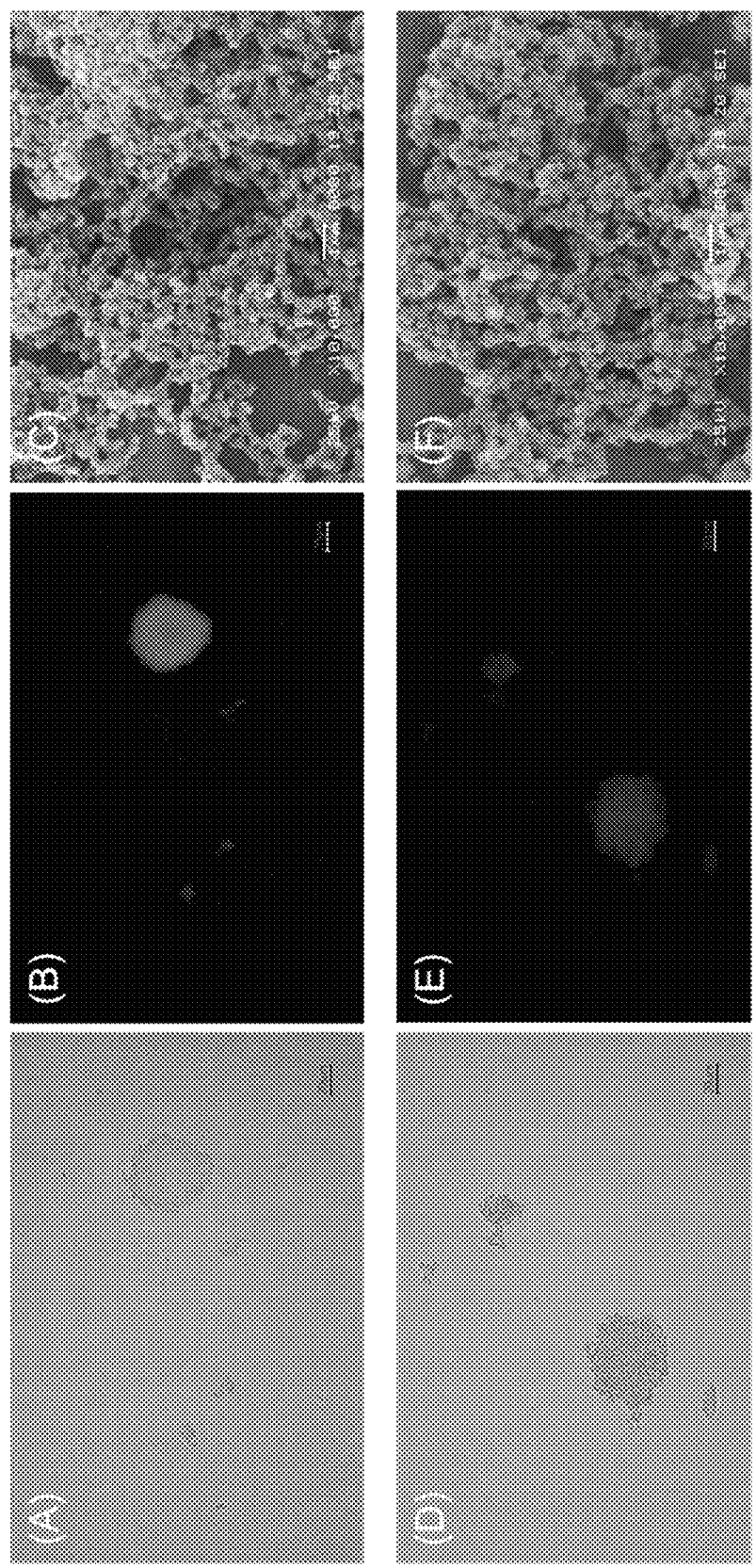

FIG. 3 shows a result of investigating the activity of a fusion protein purified from a cell lysate using silica particles. Specifically, it shows an optical image (A), a fluorescence image (B) and a scanning electron microscopic (SEM) image (C) of silica particles formed by GFP-Salp1, and an optical image (D), a fluorescence image (E) and a scanning electron microscopic (SEM) image (F) of silica particles formed by RFP-Volp1.

Figure 4:
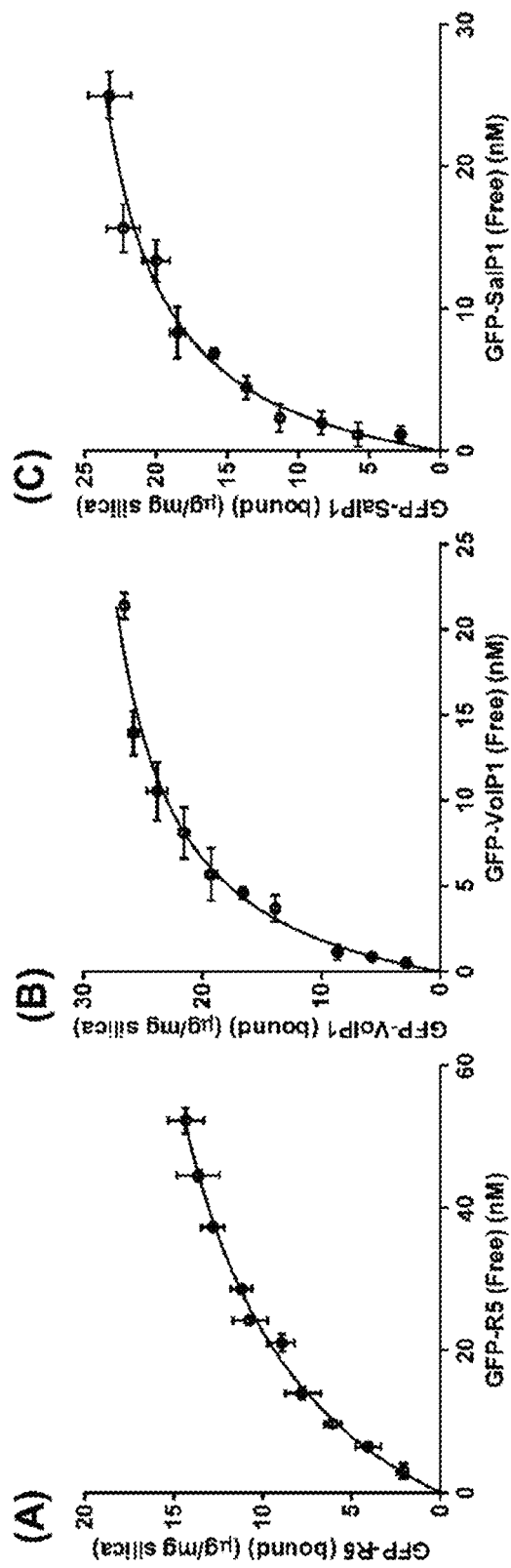

FIG. 4 shows a result of analyzing the binding affinity of (A) GFP-R5, (B) GFP-Volp1 and (C) GFP-Salp1 for silica particles. The data show results consistent with the Langmuir isotherms (solid lines) for the determination of dissociation constants ($K_d$).

Figure 5:
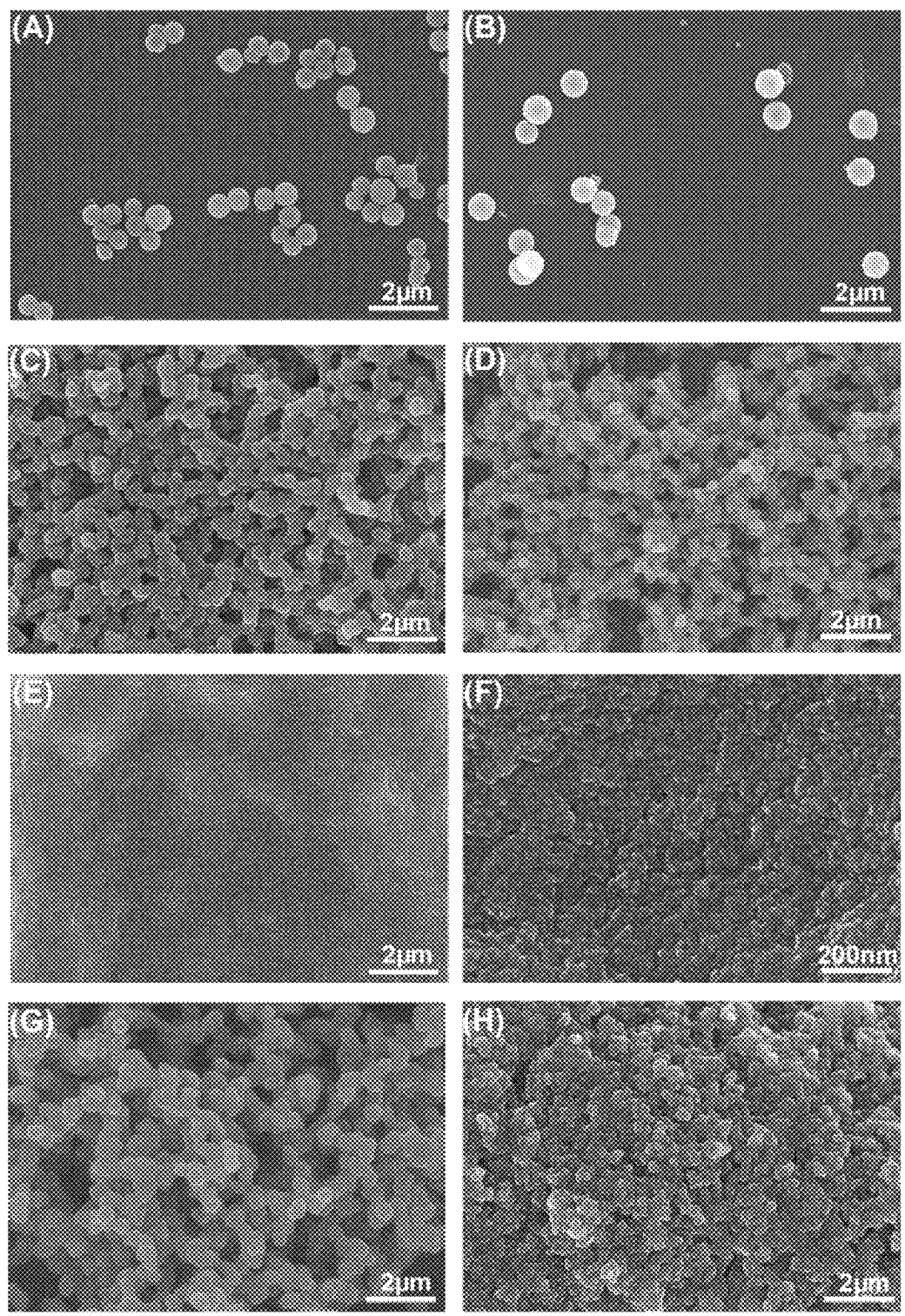

FIG. 5 shows the scanning electron microscopic (SEM) images of silica nanoparticles formed by the silica-forming peptide Salp1 (A) and Volp1 (B), silica formed by the SFP fusion protein GFP-R5 (C), GFP-Volp1 (D), GFP-Salp1 (E, F) and RFP-R5 (G), and the silica complex formed by RFP-R5 and GFP-Salp1 (H).

Figure 6:
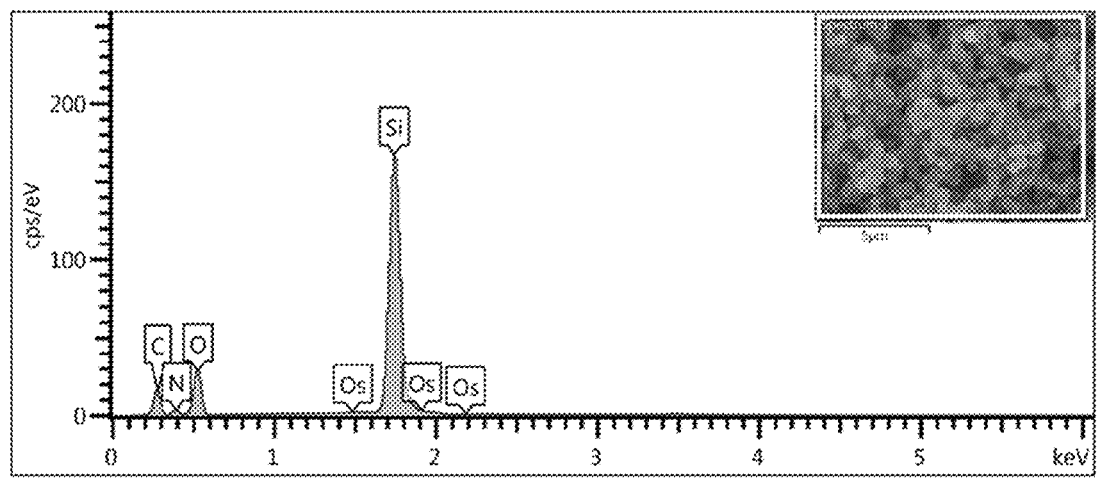

FIG. 6 shows an energy-dispersive X-ray spectroscopy (EDS) analysis result of silica particles formed by the GFP-SFP fusion protein.

Figure 7:
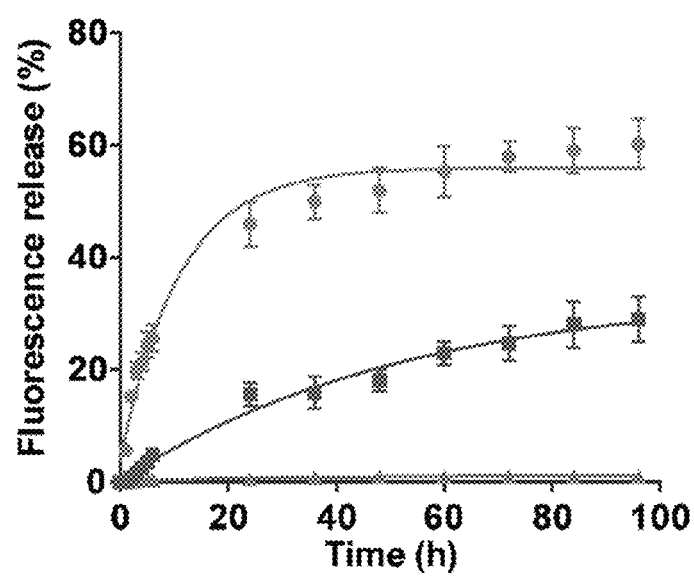
Figure 7:
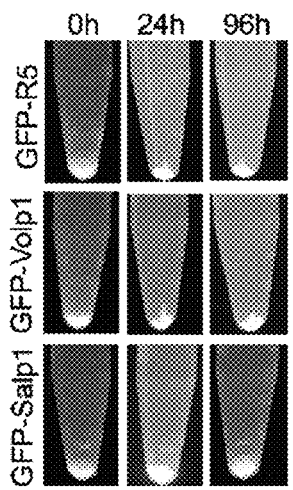

FIG. 7 (A) shows a result of encapsulating silica particles in GFP-R5 (●), GFP-Volp1 (■) and GFP-Salp1 (▲) and investigating release characteristics at pH 7.4 and room temperature in PBS. The data were averaged after measurement for 3 times. In the graphs, 100% fluorescence intensity means the fluorescence intensity for the total amount of proteins. FIG. 7 (B) shows a result of adding silica complexes in PBS and comparing fluorescence emission at 365 nm from silica particles and a supernatant 0 hour, 24 hours and 96 hours later.

Figure 8:
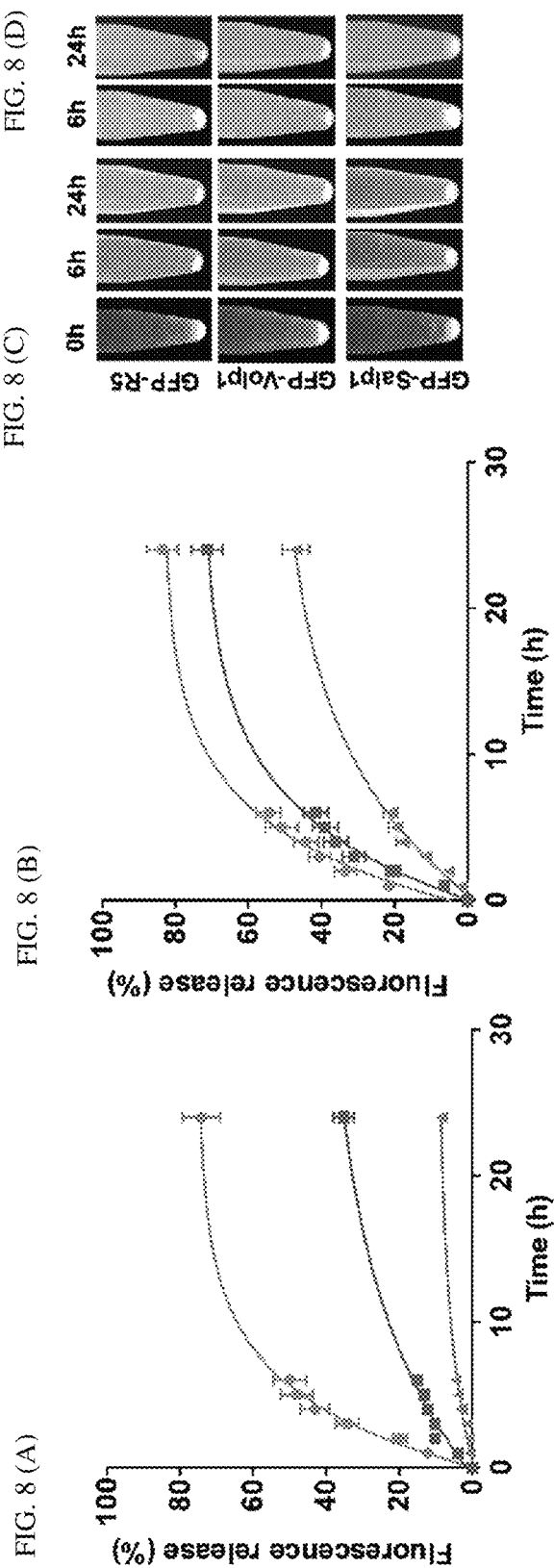

FIG. 8 (A) shows a result of comparing the rate of release of silica particles from GFP-R5 (●), GFP-Volp1 (■) and GFP-Salp1 (▲) fusion proteins by 0.25 M arginine (pH 7.4), and FIG. 8 (B) shows a result of comparing the rate of release of silica particles from GFP-R5 (●), GFP-Volp1 (■) and GFP-Salp1 (▲) fusion proteins by 1 M arginine (pH 7.4). The data were averaged after measurement for 3 times. The release amount with time was measured and 100% fluorescence intensity means the fluorescence intensity for the total amount of proteins immobilized in silica.

FIG. 8 (C) shows images obtained by reacting the silica complexes in 0.25 M arginine for 0 hour, 6 hours and 24 hours, and FIG. 8 (D) shows images obtained by reacting the silica complexes in 1 M arginine for 6 hours and 24 hours.

FIG. 9 (A) schematically shows self-encapsulation and controlled release of proteins, FIG. 9 (B) compares release of RFP-R5 (●) and GFP-Salp1 (■) from silica particles by 0.25 M arginine, and FIG. 9 (C) compares release of RFP-R5 (●) and GFP-Salp1 (■) from wet silica gel by 0.25 M arginine. The experimental condition was maintained at room temperature and pH 7.4. Average was taken after measurement for 3 times. Fluorescence emission was measured with time. 100% fluorescence intensity means the fluorescence intensity for the total amount of proteins encapsulated in silica.

FIG. 9 (D) shows the change in fluorescence emission from silica particles and a supernatant after reacting the silica particles with 0.25 M arginine for 0 hour, 6 hours and 24 hours, and FIG. 9 (E) shows the change in fluorescence emission from silica gel and a supernatant reacting the silica gel with 0.25 M arginine for 0 hour, 6 hours and 24 hours. RE: proteins released into the supernatant. R: proteins remaining in the silica matrix after reaction for 24 hours.

Figure 10:
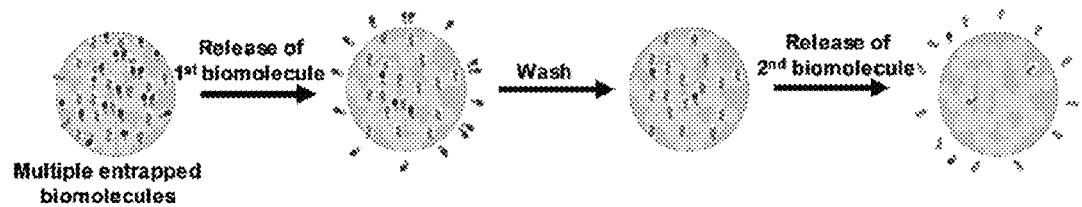
Figure 10:
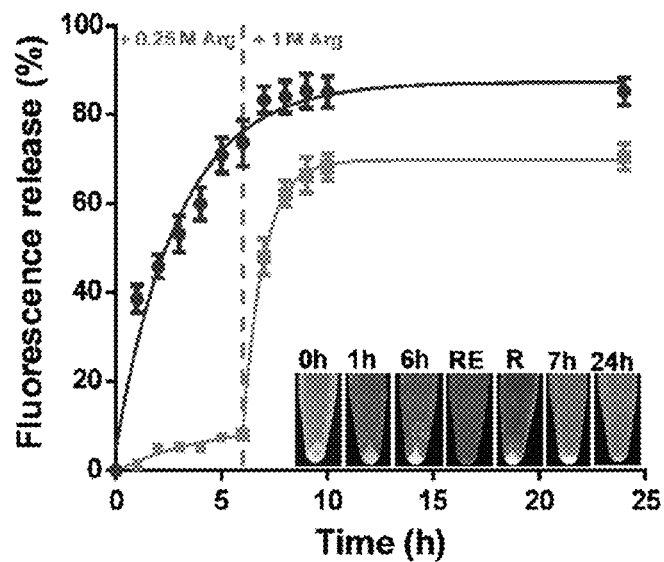

FIG. 10 (A) schematically shows the isolation of a plurality of proteins based on adsorption, and FIG. 10 (B) compares the release characteristics of RFP-R5 (●) and GFP-Salp1 (■). The silica complexes were released first by reacting with a 0.25 M arginine solution for 6 hours and then released again with a 1 M arginine solution. The experiment was conducted at room temperature and pH 7.4, and the average was taken after measurement for 3 times (RE: proteins released into supernatant after reaction for 6 hours with 0.25 M arginine. R: proteins remaining in the silica matrix after reaction with 0.25 M arginine for 6 hours).

BEST MODE

Regarding the technology of forming organic-inorganic composites and encapsulating functional biomolecules under biological environments, the preparation of biomimetic silica is drawing a lot of attentions in the fields of bioengineering and biomedicine.

Silica-forming peptides (SFP) synthesize silica from silica precursors and can form self-assembled structures during the synthesis of silica as being mediated by phosphate ion. Specifically, the amine group of SFP induces siloxane bonding by interacting with the silicic acid single molecule, leading to the formation of silica particles through the polycondensation of the silicic acid. The phosphate formed in this reaction directly affects the size and shape of the particles. In pH 7.4 Tris buffer, irregular silica particles with a rough surface are formed.

It is known that the SFP can be bound to the surface of the formed silica particles. The inventors of the present disclosure have aimed at providing a linker of SFP using the adsorption ability of SFP onto silica surface and the difference in adsorption affinity. Specifically, they have investigated the characteristics of Volp 1, Salp 1 and R5, which are new SFPs derived from marine organisms, capable of forming spherical nanosilica with the regular surface under biological environment, and have completed the present disclosure.

The inventors of the present disclosure have selected Volp 1, Salp 1 and R5 as SFPs, prepared fusion proteins wherein a fluorescent protein is bound to the N-terminal of each SFP, and investigated the characteristics of the SFPs. Specifically, they have prepared plasmid vectors wherein a green or red fluorescent protein and a Volp 1, Salp 1 or R5 silica-forming peptide gene is inserted (see Materials and methods 2), and have prepared transformants by introducing the vectors into E. coli (BL21). After inducing protein overexpression in the transformants by culturing the cells, the cells were lysed and a cell lysate was prepared by conducting centrifugation and removing cell debris (see Materials and methods 3).

Then, in order to investigate the effect of SFP on the fused target protein (fluorescent protein) and the silica adsorption ability and adsorption affinity depending on SFP, a fusion protein obtained by removing the cell debris was mixed with silica particles and incubated under room temperature/normal pressure conditions. Then, only the silica particles were separated and the adsorption efficiency to the silica particles was investigated by SDS-PAGE. In addition, the $K_d$ and $B_{max}$ values were calculated by measuring the fluorescence intensity of the silica particles. As a result, it was found out that the SFP does not affect the production and function of the bound target protein. The fusion protein was adsorbed onto the by the SFP and the adsorption efficiency of each SFP was 60% for GFP-R5, 92% for GFP-Volp1, and 90% for GFP-Salp1. It was found out that the adsorption of the fusion proteins onto silica was due to the SFP because the GFP used as a control group was not adsorbed onto the silica particles. The $K_d$ and $B_{max}$ values of each SFP were 26.27 nM and 21.64 μg for GFP-R5, 4.14 nM and 32.53 μg for GFP-Volp1, and 4.64 nM and 27.92 μg for GFP-Salp1 (see Materials and methods 4 and Experimental results 2-1 and 2-4). This result suggests that the SFP does not affect the production and function of the target protein due to a relatively short sequence and the SFP can be immobilized on the silica through non-covalent bonding.

Through this, the inventors of the present disclosure have identified the possibility of the SFP as a tag for purification of target proteins and have investigated the purity of purification of fusion proteins using silica particles (Materials and methods 3-2). As a result, it was confirmed that the SFP can be used as a tag for purifying target proteins with high purity. In addition, purity was investigated after reacting to the SFP-bound target protein with silica particles. As a result, the protein adsorption affinity was 90% in a PBST solution and 85% in a PBS solution. Therefore, it was found out that the protein can be purified with higher purity in the PBST solution (Experimental results 2-2).

Thus, the present disclosure can provide the SFP as a tag for protein purification. For the His-tag, which is conventionally used as a tag for purification, the possibility of increased protein insolubility or structural modification is reported. In addition, the imidazole used to recover protein in purification using the His-tag lowers the stability of proteins. In contrast, the protein tag of the present disclosure can solve the problem of the His-tag and improve the stability of the target protein by preventing aggregation. In addition, a purification method using the silica particles is advantageous in that it is economical since inexpensive silica is used instead of the cobalt- or nickel-functionalized resin and stability is high during storage after use.

Based on the results of the characterization of the SFPs described above (Experimental results 1), it is thought that the two cysteine residues of Salp1 serve as the branches of the peptide tag of SFP through self-crosslinking (at the tag portion) under experimental conditions. In the lysine-cysteine copolypeptide described above, the cysteine residue affects the rate and outcome of silica formation because the self-assembly of the polypeptide is affected by disulfide bonding. Thus, the inventors of the present disclosure have introduced a cysteine residue at the N-terminal of silaffin R5 and compared it with the cysteine-free R5. As a result, it was identified that the effect of the controlled release of SFP from the silica particles is enhanced by the cysteine residue introduced into R5. Accordingly, when the Salp1 containing cysteine at the N-terminal is fused with the protein, the fusion protein can be stably encapsulated in the silica gel matrix.

In addition, the inventors of the present disclosure have investigated the effect of the ionic strength of a reaction solution on silica formation. Specifically, precipitation of silica was induced by mixing the GFP-Salp1 fusion protein with pre-hydrolyzed TMOS and pH 7.4 PBS (10 mM phosphate buffer containing 150 mM NaCl). The salt played an important role in creating repulsion between the Salp1 fusion proteins, thereby initiating nucleation and leading to the formation of silica particles. For the RFP-R5 and RFP-Volp1 fusion proteins, silica was formed when the ionic strength of PBS was 0.15 M. However, for the RFP-Salp1 fusion protein, a higher ionic strength of 0.3 M was necessary for silica formation. Through this result, it was found out that protein self-encapsulation can lead to two types of convertible silica products, i.e., silica particles and silica gel, depending on ionic strength (see Experimental results 3).

In addition, the inventors of the present disclosure analyzed the release characteristics of the SFP fusion proteins. As a result, the SFP fusion proteins showed a low release rate under PBS buffer environments in contrast to the uncontrolled diffusion-based release characteristics of the existing functional biomolecules under the PBS environment. The Volp1 and Salp1 fusion proteins were released slowly from silica, and showed higher efficiency than the R5 fusion protein (see Experimental results 4-1).

Based on the fact that the arginine residue in the SFP peptide sequence plays an important role in the binding affinity for silica surface, the fusion protein encapsulated in silica was isolated using the single molecule L-arginine for controlled release of the SFP-bound fusion protein. As a result, 0.25 M arginine was more effective in interfering with the electrostatic bonding between the R5 fusion protein and silica as compared to Volp1 or Salp1. Since Volp1 and Salp1 contain more neutral arginine residues in the sequence, higher concentrations of arginine were necessary for isolation from the silica. Accordingly, 1 M arginine was used for the release of the Volp1 and Salp1 fusion proteins from the silica complex (see Experimental results 4-2).

Besides, the inventors of the present disclosure have self-encapsulated the R5 fusion protein and the Salp1 fusion protein and identified that they could be released in a controlled manner independently of each other using arginine as a trigger. Therefore, the present disclosure can provide a method for sustained release and controlled release of a target biomolecule by providing two or more SFPs having different adsorption affinity for silica as a linker for silica and the target biomolecule.

In a specific exemplary embodiment of the present disclosure, a "vector" means a DNA construct containing a DNA sequence operably linked to a suitable control sequence capable of effecting the expression of the DNA in a suitable host without particular limitation. Accordingly, the vector may be a plasmid, a phage particle, or simply a potential genomic insert. Once incorporated into a suitable host, the vector may replicate and function independently of the host genome, or may, in some instances, be integrated into the genome itself. In the present disclosure, the terms "plasmid" and "vector" are sometimes used interchangeably since the plasmid is the most commonly used form of vector and is used in the specific exemplary embodiments of the present disclosure. However, the present disclosure also includes vectors in other forms having comparable functions, which are known or to be known in the art.

Also, in the present disclosure, a "recombinant expression vector" generally means a recombinant carrier into which a heterologous DNA fragment is inserted, in general a fragment of a double-stranded DNA. Here, the heterologous DNA means a heterotype DNA, which is not naturally found in a host cell. The expression vector may be self-replicable regardless of host chromosomal DNA once in a host cell, and may produce several copies of the vector and (heterologous) DNA inserted thereinto.

The vector may contain a promoter operatively linked to a gene to be cloned. In the present disclosure, the "promoter" promotes the expression of the gene to be transfected. The promoter includes the basal element necessary for transcription and may further include an enhancer that may be used for the promotion and regulation of expression.

In the present disclosure, "transformation" or "transfection" means the introduction of DNA into a host in such a way that it becomes replicable either as an extra-chromosomal element or by chromosomal integration. The method of transformation may include any method of introducing a nucleic acid into an organism, a cell, a tissue or an organ, and may be performed by using standard techniques known in the art, depending on the host cell. Examples of the method include electroporation, protoplast fusion, calcium phosphate ($CaPO_4$) precipitation, calcium chloride ($CaCl_2$) precipitation, agitation with silicon carbide fibers, Agrobacterium-mediated transformation, PEG, dextran sulfate, lipofectamine, etc., although not being limited to that.

Since the protein expression level is different depending on the host, the host cell most suitable for the purpose may be selected and used. Examples of the host cell include prokaryotic host cells such as *Escherichia coli*, *Bacillus subtilis*, *Streptomyces*, *Pseudomonas*, *Proteus mirabilis* or *Staphylococcus*, although not being limited thereto. In addition, lower eukaryotic cells such as fungi (e.g., *Aspergillus*), yeast (e.g., *Pichia pastoris*, *Saccharomyces cerevisiae*, *Schizosaccharomyces*, *Neurospora crassa*), etc. or higher eukaryotic cells including insect cells, plant cells, mammal cells, etc. may be used as the host cell.

The silica-forming peptide of the present disclosure can be bound to the N-terminal, C-terminal, or both N-terminal and C-terminal of a protein capable of self-assembly via a ligand without effect on inherent properties, regardless of location. Therefore, in the present disclosure, a fusion protein means any fusion protein formed through binding with SFP regardless of location within a range not affecting its inherent properties.

The fusion protein may react with a silica precursor or silica to form a silica complex wherein the fusion protein is adsorbed/bound, and the fusion protein of the silica complex may exhibit different release patterns depending on the silica affinity of the SFP. The silica complex may be provided as a drug delivery system capable of controlled drug release based on the difference in silica affinity of the SFP and the difference in release pattern resulting therefrom. The silica complex provided as a drug delivery system may include two or more SFPs having a different affinity for silica. The respective SFPs may be bound to the same or different drugs such that the drug is released from the silica complex according to the release pattern of the SFPs.

The drug delivery system of the present disclosure may further include a pharmaceutically acceptable carrier, and the silica complex of the drug delivery system may have a core-shell structure in which a pharmaceutically active ingredient can be included.

The pharmaceutically acceptable carrier includes a carrier and a vehicle commonly used in the field of medicine. Specifically, it includes an ion-exchange resin, alumina, aluminum stearate, lecithin, a serum protein (e.g., human serum albumin), a buffer (e.g., phosphate, glycine, sorbic acid, potassium sorbate, partial glyceride mixture of saturated vegetable fatty acid), water, a slat, an electrolyte (e.g., protamine sulfate, disodium hydrogen phosphate, potassium hydrogen phosphate, sodium chloride and zinc salt), colloidal silica, magnesium trisilicate, polyvinylpyrrolidone, a cellulose-based substrate, polyethylene glycol, sodium carboxymethylcellulose, polyacrylate, wax, polyethylene glycol, wool fat, etc., although not being limited thereto.

In addition, the drug delivery system of the present disclosure may further include, in addition to the above-described ingredients, a lubricant, a wetting agent, an emulsifier, a suspending agent, a preservative, etc.

Hereinafter, the present disclosure will be described in detail through examples. However, the following examples are for illustrative purposes only and it will be apparent to those of ordinary skill in the art that the scope of the present disclosure is not limited by the examples. The present disclosure can be changed variously and may have various exemplary embodiments. Hereinafter, the specific exemplary embodiments will be illustrated in described in detail. However, the present disclosure is not limited by the specific exemplary embodiments, and it should be understood that the present disclosure includes all modifications, equivalents and alternatives included in the idea and technical scope thereof. In the description of the present disclosure, when it is determined that a specific description of the related known technology unnecessarily obscures the gist of the present disclosure, a detailed description thereof will be omitted.

MATERIALS AND METHODS

1. Materials

Volp1 and Salp1 peptides (10 mg) were synthesized by Genescript (Piscataway, N.J., USA).

Tetramethyl orthosilicate (TMOS) was used as a silica precursor and was purchased from Sigma Aldrich (St. Louis, Mo., USA). Silica particles (0.8 μm) were purchased from Kojundo Chemical Laboratory (Saitama, Japan). All the reagents used in the following experiments were of analytical grade.

2. Construction of Recombinant Plasmid

For the construction of SFP fusion proteins, a pUC57 vector wherein a Volp1 or Salp1 sequence was introduced between BamHI and AvrII was synthesized. In order to transfer the SFP sequence to a protein expression vector, the BamHI-AvrII sites were cleaved by treating with restriction enzymes and then inserted into a pETDuet-1 (Novagen) plasmid. The vectors were named as pET-Volp1 and pET-Salp1.

Subsequently, the mut-3 green fluorescent protein (GFP) sequence was amplified by PCR and then inserted at the BamHI-PstI sites of the pET-SFP plasmid including the SFP sequence such that the Volp1 or Salp1 sequence was fused at the C-terminal of the GFP. The vectors were named as pET-GFP-Volp1 and pET-GFP-Salp1.

For use as a control group, a pET-GFP vector was constructed by amplifying the same GFP sequence by PCR and then inserting at the BamHI-XhoI sites of the pET-Duet-1 plasmid.

Then, vectors wherein SFP was fused at the C-terminal of a red fluorescent protein (RFP) instead of the GFP were constructed in the same manner as the construction of the pET-GFP-(Volp1 or Salp1) vector. The vectors were named as pET-RFP-R5, pET-RFP-Volp1 and pET-RFP-Salp1.

3. Expression and Purification of Recombinant Protein 3-1. Expression of Recombinant Protein The plasmid including GFP, GFP-SFPs, RFP or RFP-SFPs was transformed into *E. coli* BL21 (DE3) for expression. *E. coli* was cultured at 37°, in LB medium, and 0.5 mM IPTG (isopropyl-β-D-thiogalactopyranoside) was added when $OD_{600}$ reached 0.4. Then, protein overexpression was induced by culturing the cells at 28° C. for 6 hours. After the culturing, a pellet was obtained by centrifuging the cells at 5000×g for 5 minutes.

For purification of the protein, the cell pellet was suspended in 25 mM Tris-HCl buffer (pH 8.0) containing 150 mM NaCl, 10 mM imidazole, 1% glycerol, 10 μL protease inhibitor cocktail (X100) (Thermo Scientific, Rockford, Ill., USA) and 10 μL 25 U DNase. The cells were lysed using a sonicator and then centrifuged at 4° C. and 20000×g for 30 minutes in order to remove the cell debris.

3-2. Purification of Recombinant Protein (1) Purification using histidine tag: The protein supernatant having a histidine tag at the N-terminal was adsorbed by adding to a HisPur nickel resin column. The column was washed with Tris-HCl buffer (pH 8.0) containing 150 mM NaCl, 1% glycerol and 20 mM imidazole in order to remove impurities other than the adsorbed protein. In order to obtain the target protein, extraction was conducted using Tris-HCl buffer (pH 8.0) containing 150 mM NaCl, 1% glycerol and 200 mM imidazole.

(2) Purification using silica particles: The cell pellet wherein the SFP (Volp1, Salp1) fusion protein was overexpressed was suspended in an adsorption buffer (25 mM sodium phosphate buffer (pH 6-6.5) or 25 mM Tris-HCl buffer (pH 7-8.5) with 0.1% (v/v) Tween 20). After sonication, the supernatant of a cell lysate was obtained by centrifuging at 20,000×g for 40 minutes. The cell lysate was adsorbed onto 30 mg of silica particles by shaking for 10 minutes. Then, protein-adsorbed silica particles were obtained by conducting centrifugation at 8,000×g for 10 minutes. After elution of the protein-adsorbed silica particles with 1 mL of 25 mM Tris-HCl buffer (pH 8.5) containing 1 M arginine, a protein-containing supernatant was obtained by conducting centrifugation at 8,000×g for 2 minutes.

3-3. Purity of Purified Recombinant Protein

The purity of the SFP fusion protein was investigated by SDS-PAGE. After analysis of size and purity, the protein was transferred to an experimental buffer through dialysis and then concentrated using the Amicon centrifugal filter (Millipore, Billerica, Mass., USA). The concentration of the protein was measured by the Bradford assay (Bio-Rad protein assay kit, Bio-Rad, Hercules, Calif., USA).

4. Calculation of Dissociation Constant ($K_d$) of GFP-SFP Fusion Protein

In order to measure the adsorption strength between the purified GFP-SFP fusion protein and silica particles, the GFP-R5, GFP-Volp1 and GFP-Salp1 fusion proteins were prepared with concentrations of 10-100 nM in 1 mL of PBS (pH 7.4). The protein was mixed and reacted with 0.1 mg of silica particle for 10 minutes and then centrifuged at 15,000×g for 2 minutes. The amount of the protein adsorbed onto the silica particles was measured from the difference in the GFP fluorescence emission intensity of the initially added protein and in the GFP fluorescence emission intensity of the supernatant remaining after the reaction. GraphPad Prism (GraphPad Software Inc., La Jolla, Calif., USA) program was used for computation. The result corresponded to the Langmuir adsorption isotherms that determine the $K_d$ and $B_{max}$ values.

5. Preparation and Characterization of Silica Complex

For analysis of peptide-based silica formation, silica formation was induced at room temperature by mixing 80 mM sodium phosphate buffer (pH 7.4), 100 mM hydrolyzed TMOS and 0.5 mM peptide. The formed silica precipitate was recovered after centrifuging at 15,000×g for 2 minutes and then washing 3 timed with triply distilled water. As a negative control group, reaction was conducted without the biomolecule.

For the characterization of the silica, the synthesized silica precipitate washed with triply distilled water and then dried at room temperature for 12 hours. The shape and composition of the silica were analyzed by scanning electron microscopy (SEM) and energy-dispersive X-ray spectroscopy (EDS) (KBSI Jeonju Center).

6. Analysis of Secondary Structure by Circular Dichroism Spectroscopy

Circular dichroism (CD) spectroscopic analysis was conducted using the Jasco J-1500 CD spectrophotometer (Jasco Inc., Easton, Md., USA) at the Korea Basic Science Institute Ochang Center. After preparing 0.2 mg/mL Volp1 and Salp1 in 50 mM phosphate buffer (pH 7.4), the change in secondary structure depending on the presence of 1 mM hydrolyzed TMOS was measured. The analysis was conducted at room temperature in the UV range of 190-260 nm.

7. Measurement of SFP Fusion Protein Released from Silica Particles

Sol-gel silica formation was conducted using the recombinant protein as described above. The silica product was washed 3 times with triply distilled water to remove impurities. For the protein release experiment, the silica particles in which the GFP-SFP fusion protein was encapsulated were suspended in 1-mL solutions of different conditions (PBS or pH 7.4 buffer containing 0.25-1 M L-arginine). The experiment was conducted in triplicates to ensure accuracy. The reaction was conducted by agitating a tube containing the SFP-fused silica and the buffer at room temperature at a rate of 150 rpm. After a predetermined time, 100 μL of the sample was taken and then centrifuged for 2 minutes at 15,000×g. The fluorescence emission by GFP was measured the centrifuged supernatant using a fluorescence reader (Infinite F200 NanoQuant, Tecan, Austria). After the measurement was made, the sample was returned to the test tube to avoid volume loss. The result was consistent with the exponential decay model.

For immobilization of a plurality of proteins, the RFP-R5 fusion protein and the GFP-Salp1 fusion protein were mixed each at 50 μM. Then, silica polymerization was induced by mixing with 100 mM hydrolyzed TMOS and 50 mM phosphate buffer or pH 7.4 PBS. The formed silica precipitate was washed with triply distilled water to remove impurities. For measurement of protein release, the silica complex was suspended in 1 mL of a 0.25 M L-arginine solution (pH 7.4) and then the fluorescence intensity of the released protein was measured from the supernatant with time as described earlier.

In the experiment of releasing proteins from the silica complex wherein a plurality of proteins are encapsulated, the silica complex wherein RFP-R5 and GFP-Salp1 are encapsulated was suspended in 1 mL of a 0.25 M L-arginine solution (pH 7.4) and the fluorescence intensity of the supernatant was measured after a predetermined time (step 1). Then, after conducting centrifugation for 2 minutes at 15,000×g, the silica particles were recovered and washed 3 times with 10 mM Tris-HCl (pH 7.4). For the step 2 release, the silica particles were reacted with a 1 M L-arginine solution (pH 7.4) and the amount of released protein was measured with time.

EXPERIMENTAL RESULTS

1. Characteristics of the Silica-Forming Peptide (SFP)

The sequence and molecular characteristics of the Volp1, Salp1 and R5 peptides synthesized by Genescript are described in Table 1.

TABLE 1

| SFP | (aa) | Peptide sequence | Molecular weight (Da) | Net charge at pH 7.4 | PI value | Hydrophobicity (Kcal * mol$^{-1}$) |
|---|---|---|---|---|---|---|
| R5 | 19 | SSKKSGSYSGSKGSKRRIL | 2013.28 | +6 | 11.22 | +26.31 |
| Volp1 | 15 | SGRRRGSRRRGSRRR | 1856.09 | +9 | 12.91 | +29.02 |
| Salp1 | 20 | CGRRRGGRGGRGRGGCGRRR | 2143.45 | +9 | 12.30 | +34.50 |

2. Preparation and Characterization of Recombinant Protein Adsorbed onto Silica Particles 2-1. Adsorption Ability of Recombinant Protein for Silica Particles First, in order to investigate whether the SFP is adsorbed onto silica particles, SFP-fused proteins were prepared by introducing the R5, Volp1 and Salp1 peptides into green fluorescent protein (GFP). E. coli was incubated with the SFP-fused fluorescent proteins or a fluorescent protein to be used as a control group and then lysed. The E. coli lysate was mixed with silica particles to induce adsorption at room temperature. The protein adsorbed onto the silica particles was recovered together with the silica particles through centrifugation and then washed several times with pH 7.4 PBST buffer to remove impurities and non-specifically bound substances. The protein adsorbed onto the silica particles was extracted using Laemmli SDS sample buffer and then analyzed by SDS-PAGE. The adsorption efficiency onto the silica particles was calculated through gel band analysis. As a result, the adsorption efficiency was 60% for GFP-R5, 92% for GFP-Volp1, and 90% for GFP-Salp1. The GFP used as a control group showed no binding ability for silica.

From this result, it was confirmed that the protein fused with Volp1 and Salp1 showed stronger adsorption affinity for silica than the R5-fused protein.

Figure 1:
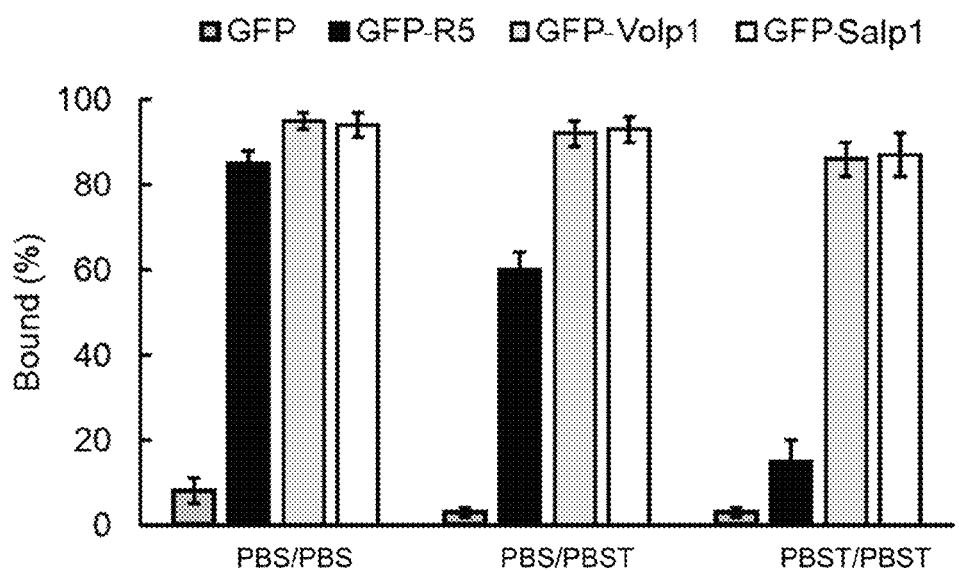
FIG. 1 compares the adsorption affinity of a GFP-SFP fusion protein for silica depending on reaction conditions.

2-2. Adsorption Ability of Recombinant Protein for Silica Particles Depending on Reaction Solution Then, in order to obtain proteins with higher purity, silica adsorption was induced while minimizing non-specific adsorption of E. coli proteins using PBST containing 0.1% Tween 20. As a result, the Volp1 and Salp1 fusion proteins showed a high adsorption affinity of about 90% even after washing with the PBST solution after the adsorption in PBST (PBST/PBST). In contrast, whereas GFP-R5 showed adsorption affinity of 85% when washed with PBS after adsorption in PBS (PBS/PBS), the adsorption affinity was decreased to about 15% when washed with PBST after adsorption in PBST (PBST/PBST) (FIG. 1).

2-3. Purity of Recombinant Protein Purified Using Silica Particles

Then, in order to investigate the purity of the purification method using silica particles and Volp1 and Salp1, the GFP-Salp1 and RFP-Volp1 fusion proteins were purified and analyzed by SDS-PAGE. As a result, the purity of GFP-Salp1 and RFP-Volp1 was 90% and 89%, respectively. The 20-kDa band (arrow) of RFP-Volp1 was due to the partial hydrolysis of N-acylimine in the RFP during the heating of the protein for SDS-PAGE (FIG. 2). Additionally, in order to investigate the activity of proteins purified using the silica particles, the silica-forming ability of and fluorescence emission from the GFP-Salp1 and RFP-Volp1 fusion proteins were investigated. As a result, the fusion proteins formed silica within several seconds when mixed with 100 mM TMOS in pH 7.6 PBS, and exhibited fluorescence emission due to stable self-encapsulation (FIG. 3).

The GFP and the GFP-SFP fusion protein used for the self-encapsulation experiments of silica were prepared by adding the histidine tag for purification to the N-terminal of the proteins.

As a result, the proteins wherein Volp1 or Salp1 are fused at the C-terminal of the GFP showed no difference in fluorescence emission from the GFP prepared as a control group.

From this result, it was confirmed that Volp1 and Salp1, which are short peptide linkers fused at the C-terminal of the GFP, has no significant effect on the activity of the protein.

When the degree of adsorption to the silica particles was analyzed under PBS buffer environment using the purified GFP-SFP, the result consisted with the Langmuir isotherms (FIG. 4).

2-4. Adsorption Strength of Recombinant Protein for Silica Particles

The silica adsorption $K_d$ values of GFP-R5, GFP-Volp1 and GFP-Salp1 were calculated as 26.27, 4.14 and 4.64 nM, respectively. The maximum adsorption amount of GFP-R5, GFP-Volp1 and GFP-Salp1 for 1 mg of silica particles was 21.64, 32.53 and 27.92 µg, respectively. This result is consistent with the $K_d$ values for the synthetic R5 peptide and other silica-binding affinity tags.

3. Self-encapsulation of GFP-SFP Fusion Protein by Silica Formation

First, it was investigated whether the synthesized Volp1 and Salp1 peptides catalyze silica polymerization like silaffin R5 as reported. Both peptides formed silica precipitates within about 5 minutes at room temperature when mixed with silicic acid under pH 7.4 phosphate buffer environment. The precipitates were observed as uniformly distributed spherical silica nanoparticles with a size of 580±82 nm. No precipitate was formed in the absence of the peptide (FIG. 5, (A) and (B)).

Then, it was investigated through CD spectroscopy whether the Volp1 and Salp1 peptides form secondary structures or whether the secondary structure is changed during the reaction with silicic acid. Both peptides showed random coil structures at pH 7.4, similarly to R5, and showed no structural change upon reaction with silicic acid.

Then, in order to encapsulate the GFP-SFP fusion protein in silica, 100 µM of the purified protein was reacted with 100 mM TMOS in phosphate buffer. GFP-R5 and GFP-Volp1 formed silica precipitates quickly within 20 minutes at room temperature. The formation of silica particles with a size of 410±60 and 250±43 nm was observed in SEM analysis for GFP-R5 and GFP-Volp1, respectively (FIG. 5, (C) and (D)). However, silica precipitate was not formed for GFP-Salp1 and GFP. In addition, the reaction product of silicic acid and GFP-Salp1 was unexpectedly observed as a wet silica gel, not as particles. GFP-Salp1 or GFP resulted in a wet silica gel in which small particles with a size of 17±4 nm are aggregated through self-encapsulation after reaction with silicic acid for 2 hours (FIG. 5, (E) and (F)). For GFP-R5, GFP-Volp1 and GFP-Salp1, the adsorption efficiency onto silica by self-encapsulation was 88±4%, 92±3% and 94±3%, respectively. For His-tagged GFP with no SFP, about 52% was self-encapsulated. However, unlike the SFP-fused GFP, continued loss of protein from silica was observed during the washing step. From this result, it was confirmed that the SFP serves as an affinity tag for silica and allows the fused protein to be immobilized strongly onto the silica matrix.

As a result of EDS (energy dispersive X-ray spectroscopic) analysis, the silica particles formed by GFP-SFP contained Si, O, C and N in that order (FIG. 6). The presence of C and N reveals that the silica forms an organic-inorganic composite including the SFP fusion protein.

4. Release Characteristics of GFP-SFP Fusion Protein from Silica

4-1. Release Characteristics Depending on SFP

In order to investigate whether SFP can function as a protein fusion tag to allow the controlled release of a protein from silica, the GFP-R5, GFP-Salp1 and GFP-Volp1 fusion proteins were adsorbed onto silica nanoparticles and the amount of the fluorescent protein released from the silica nanoparticles into a supernatant was measured.

As a result of measuring the amount of the fluorescent protein released into pH 7.4 PBS, the protein release amount was 25% at 6 hours, 46% at 24 hours and 60.50% at 96 hours, for GFP-R5. This is consistent with the release characteristics of GFP-R5 mentioned above. However, for the GFP-Volp1 fusion protein, the release amount was only 5% at 6 hours, 15% at 24 hours and 29% at 96 hours due to high stability after adsorption onto silica particles. Meanwhile, GFP-Salp1, which is in the form of a silica gel, showed no protein release into the supernatant even 96 hours later (FIG. 7).

4-2. Release Characteristics Depending on Concentration of L-arginine

Then, the adsorption affinity of the SFP fusion proteins for silica was investigated by conducting release experiments using two L-arginine solutions (pH 7.4) of different concentrations. Interestingly, the 0.25 M arginine solution served as a trigger that accelerates release of the fusion protein from silica (FIG. 8, (A) and (C)). About 50% of GFP-R5 was released 6 hours later, and 74% was released 24 hours later. In comparison, GFP-Volp1 and GFP-Salp1 showed higher silica affinity. GFP-Volp1 showed 35% of release from silica 24 hours later, and GFP-Salp1 showed less than 10% of release 24 hours later.

Then, it was investigated whether the arginine solution at a high concentration of 1 M can serve as a trigger to release Volp1 and Salp1 (FIG. 8, (B) and (D)). For GFP-R5, there was no significant difference in release characteristics when 1 M arginine or 0.25 M arginine was used. However, for Volp1 and Salp1, there was significant difference in protein release for 0.25 M arginine and 1 M arginine. In 1 M arginine, the release of GFP-Volp1 and GFP-Salp1 was 41% and 20% at 6 hours, respectively, and 71% and 47% at 24 hours, respectively. It is to be noted that the biological activity of the GFP fusion protein is maintained intact while it is released after being self-encapsulated in silica.

5. Controlled Release of Proteins Encapsulated in Silica 5-1. Preparation of Silica Complex Containing a Plurality of SFPs It was expected that a plurality of proteins encapsulated together in silica using different SFPs would be released at different rates depending on the properties of the SFPs. To this end, a silica complex wherein different fluorescent proteins are bound to the SFP fusion protein was prepared by mixing GFP-Salp1 and RFP-R5 or GFP-R5 and RFP-Salp1 with pre-hydrolyzed 50 μM TMOS (FIG. 5 (H)). The prepared silica particle developed a light orange color. It was confirmed that GFP and RFP are encapsulated uniformly in the silica complex (FIG. 9 (D)).

5-2. Controlled Release of Proteins Encapsulated in Silica

Only the R5 fusion protein was released by 0.25 M arginine (pH 7.4). In contrast, the Salp1 fusion protein remained encapsulated in the silica particles under the same condition.

Next, it was investigated whether the release of a plurality of proteins from silica can be controlled using SFP. GFP-Salp1 and RFP-R5 are encapsulated in different forms as wet silica gel and silica particles, respectively. As confirmed earlier, RFP-R5 exists in the silica complex in the form of silica particles and is released gradually by 0.25 M arginine for 24 hours. However, GFP-Salp1 is hardly released even 24 hours later. The RFP-R5 existing as silica particles can be released more easily than the GFP-Salp1 existing as silica gel. It is because protein release is easier from dispersed silica than from the silica gel network. Accordingly, although RFP-R5 was released mostly over 6 hours, the green GFP-Salp1 remained in the silica precipitate (FIG. 9, (B) and (D)). From this result, it can be seen that the Salp1 fusion protein remains stable as being encapsulated in the silica matrix during the experiment.

Finally, it was investigated whether proteins having different silica affinity can be released in a controlled manner by the SFP tag. After forming a silica complex using GFP-Salp1 and RFP-R5 together, only the RFP-R5 was released using 0.25 M arginine (pH 7.4) as a trigger. After washing the remaining silica precipitate, the GFP-Salp1 was released using 1 M arginine (pH 7.4) as a trigger. As a result, the two proteins encapsulated in the same silica complex could be released separately using the two solutions (FIG. 10).

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A linker composition comprising two or more silica-forming peptides having different affinity for silica,
   wherein the silica-forming peptide is a peptide selected from a group consisting of: a peptide comprising an amino acid sequence of SEQ ID NO 1; a peptide comprising an amino acid sequence of SEQ ID NO 2; and a peptide comprising an amino acid sequence of SEQ ID NO 3, and
   wherein N-terminal of at least one of the silica-forming peptide is bound to a red fluorescent protein.

2. The linker composition according to claim 1, wherein the composition is used for isolation and purification of a substance bound to the silica-forming peptide.

3. The linker composition according to claim 1, wherein the composition is used for control of the release of a substance bound to the silica-forming peptide.

* * * * *

SEQUENCE LISTING

```
<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: silica forming peptide_R5

<400> SEQUENCE: 1

Ser Ser Lys Lys Ser Gly Ser Tyr Ser Gly Ser Lys Gly Ser Lys Arg
1               5                   10                  15

Arg Ile Leu

<210> SEQ ID NO 2
<211> LENGTH: 15
<212> TYPE: PRT
<213> ORGANISM: Artificial Sequence
<220> FEATURE:
<223> OTHER INFORMATION: silica forming peptide_Volp1

<400> SEQUENCE: 2

Ser Gly Arg Arg Arg Gly Ser Arg Arg Arg Gly Ser Arg Arg Arg
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: silica forming peptide_Salp1

<400> SEQUENCE: 3

Cys Gly Arg Arg Arg Gly Gly Arg Gly Gly Arg Gly Arg Gly Gly Cys
1               5                   10                  15

Gly Arg Arg Arg
            20
```